United States Patent [19]

Greenland

[11] Patent Number: 4,576,594
[45] Date of Patent: Mar. 18, 1986

[54] VENTED DRIP CHAMBER FOR USE WITH A SYRINGE

[75] Inventor: John S. Greenland, Encinitas, Calif.

[73] Assignee: Warner-Lambert Company, Morris Plains, N.J.

[21] Appl. No.: 634,838

[22] Filed: Jul. 26, 1984

[51] Int. Cl.$^4$ .............................................. A61M 5/16
[52] U.S. Cl. ..................................... 604/251; 604/241
[58] Field of Search .............................. 604/251–255, 604/405, 187, 240, 241

[56] References Cited

U.S. PATENT DOCUMENTS

| | | | |
|---|---|---|---|
| 2,833,281 | 5/1958 | Krug | 128/221 |
| 3,316,908 | 5/1967 | Burke | 128/214 |
| 3,323,774 | 6/1967 | Wilson | 604/251 X |
| 3,359,977 | 12/1967 | Burke | 128/214 |
| 3,542,024 | 11/1970 | Burke | 604/241 |
| 3,542,240 | 11/1970 | Solowey | 222/83 |
| 3,795,558 | 3/1974 | Dabney et al. | 156/73 |
| 3,797,521 | 3/1974 | King | 137/525.7 |
| 3,822,700 | 7/1974 | Pennington | 128/214 C |
| 3,938,520 | 2/1976 | Scislowicz et al. | 128/272.3 |
| 4,262,671 | 4/1981 | Kersten | 128/272.3 |

FOREIGN PATENT DOCUMENTS 2877238 7/1977 Fed. Rep. of Germany .

OTHER PUBLICATIONS

Advertising Brochure–Quest Medical, Inc., 1984.

*Primary Examiner*—Stephen C. Pellegrino
*Attorney, Agent, or Firm*—Neil K. Nydegger

[57] ABSTRACT

A vented drip chamber, threadably engageable with a fluid filled hypodermic syringe, comprises an adapter having dual passageways. A first passageway allows fluid communication between the syringe and the drip chamber while the second passageway provides an air vent from outside the drip chamber to the syringe. The second passageway further comprises a cannula which extends into the fluid upon attachment of the drip chamber with the syringe. A ball valve which is disposed in the second passageway allows air to flow into the syringe to replace the dispensed fluid, but does not allow fluid to flow from the syringe through the second passageway.

15 Claims, 4 Drawing Figures

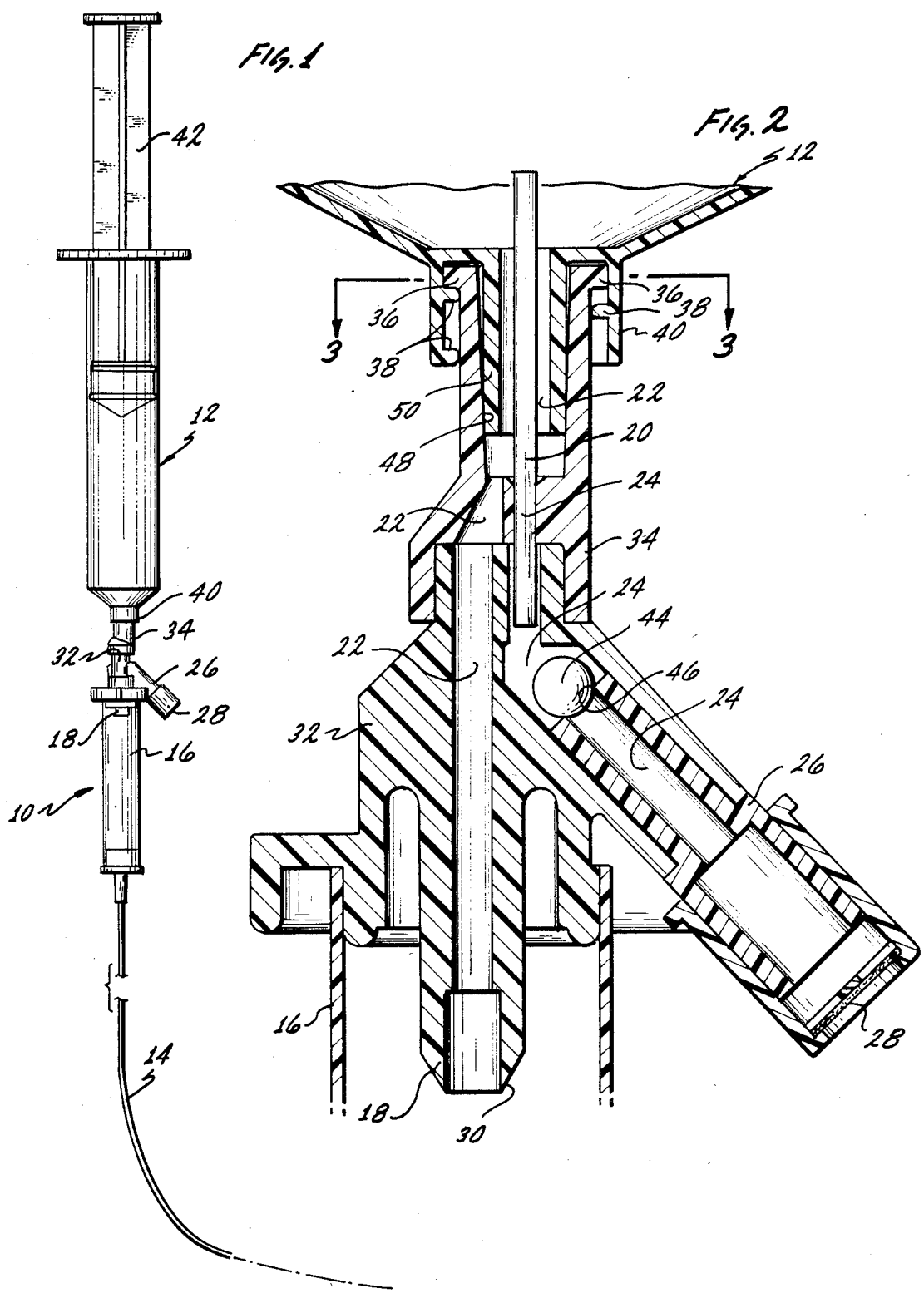

VENTED DRIP CHAMBER FOR USE WITH A SYRINGE

BACKGROUND OF THE INVENTION

This invention relates generally to vented drip chambers used for administration of IV solutions to patients. More particularly, this invention relates to an attaching means between a drip chamber and an air-tight fluid source to permit venting of the fluid source during flow of fluid from the source to the drip chamber. This invention is particularly, though not exclusively, useful for the administration of IV solutions to a patient through a drip chamber from a fluid source such as a hypodermic syringe.

DESCRIPTION OF THE PRIOR ART

In numerous health care situations, there is a need to intravenously administer precise quantities of a particular fluid medicament to a patient over an extended period of time. Furthermore, the precise quantities of fluid medicament are often needed in only small quantities for a one-time infusion. On such occasions, the use of large or bulky IV bottles or bags are ineffective, awkward and inconvenient.

A solution to this problem is to use standard hypodermic syringes as the fluid source container. Generally, such syringes are readily available and provide an effective means for the precise measurement of small fluid quantities. Syringes, however, are typically operated by hand and this can be inconvenient when infusion over an extended period of time is required. Under such circumstances, use of an IV administration set may be more appropriate. Thus, there is a need to somehow incorporate the use of a hypodermic syringe with the use of an IV administration set.

Whenever an administration set is used, it is particularly important there be some visual indication of fluid flow in the set. Typically, a drip chamber is used for this purpose. Thus, if a syringe is used to collect a precisely measured amount of fluid medicament to be administered to a patient, there is a need for a drip chamber that can be attached directly to the syringe.

The use of a syringe in an administration set may be particularly appropriate when a "piggyback" system is desired. More particularly, as will be appreciated by those skilled in the art, the drip chamber of the present invention is well suited for incorporation into a piggyback system such as the one disclosed in U.S. Pat. No. 4,533,347 which is assigned to the same assignee of record as the present invention.

When a syringe is required for the above purposes, the engagement means between syringe and drip chamber must overcome certain inherent problems. Firstly, fluid filled syringes are typically air-tight. Thus, they must be vented if fluid is to flow therefrom in a regular and predictable manner. Secondly, the dispensing nozzle of a syringe is typically of such a reduced cross-sectional area that fluid and venting air cannot flow therethrough simultaneously. Therefore, there is a need to provide separate passageways for fluid flow and for venting air flow. Preferably, as in the present invention, the necessarily simultaneous flow of fluid and venting air can be accomplished through the dispensing nozzle of the syringe without alteration or modification of the syringe.

Well known in the art are vented drip chambers with attaching means of the type disclosed in U.S. Pat. No. 3,316,908 to Burke in which a spike is used to connect the drip chamber to the fluid source. Such devices, however, do not permit attachment of the drip chamber to a hypodermic syringe or other fluid container having a threadable luer lock attachment means. Also well known in the art are devices such as disclosed in U.S. Pat. No. 3,822,700 to Pennington wherein a vented means for attaching drip chambers to a fluid source has an additional passageway for the addition or withdrawal of fluids from the fluid source. In these devices, however, a spike is used to effect engagement of the drip chamber with the fluid source. There is, therefore, still the need for a vented drip chamber which is engageable with a standard hypodermic syringe or with any fluid container which must be accessed by some means other than through a spike penetrable stopper.

Accordingly, it is an object of the present invention to provide a vented drip chamber which is engageable with an air-tight fluid container having a standard threadable luer type engagement access means. Still another object of this invention is to provide an easy-to-use, relatively inexpensive disposable drip chamber which can be easily attached to a hypodermic syringe to visually monitor the flow of a precisely measured amount of fluid medicament through an IV administration system to a patient.

SUMMARY OF THE INVENTION

The preferred embodiment of this invention includes an adapter associated with a standard drip chamber having dual passageways therethrough. One of the passageways provides means for fluid communication between a fluid container and a drop former in the drip chamber. The second passageway includes a cannula which extends from the adapter and which is insertable into the body of fluid contained within the container to vent air for the fluid container. Formed on the adapter is a luer-type engagement having means for threadably connecting the drip chamber with the fluid source.

The novel features of this invention, as well as the invention itself, both as to its organization and operation will be best understood from the accompanying drawings, taken in conjunction with the accompanying description, in which similar reference characters refer to similar parts, and in which:

BRIEF DESCRIPTION OF THE DRAWINGS

FIG. 1 is a front elevational view of the vented drip chamber in connection with a hypodermic syringe;

FIG. 2 is a cross-sectional view of a portion of the vented drip chamber and syringe with portions broken away for clarification;

DESCRIPTION OF THE PREFERRED EMBODIMENT

Referring now in detail to the drawings, the vented drip chamber of the present invention, generally designated 10, is shown in operative connection with a syringe 12 in FIG. 1. As seen in FIG. 1, the drip chamber 10 is used as part of an IV administration set between a fluid source, such as the syringe 12, and an IV tube 14.

When so used, drip chamber 10 permits visual inspection of fluid flow in the system as IV fluid passes through the IV tube 14 and into a pump or controller (not shown) for subsequent infusion into a patient.

Figure 4:
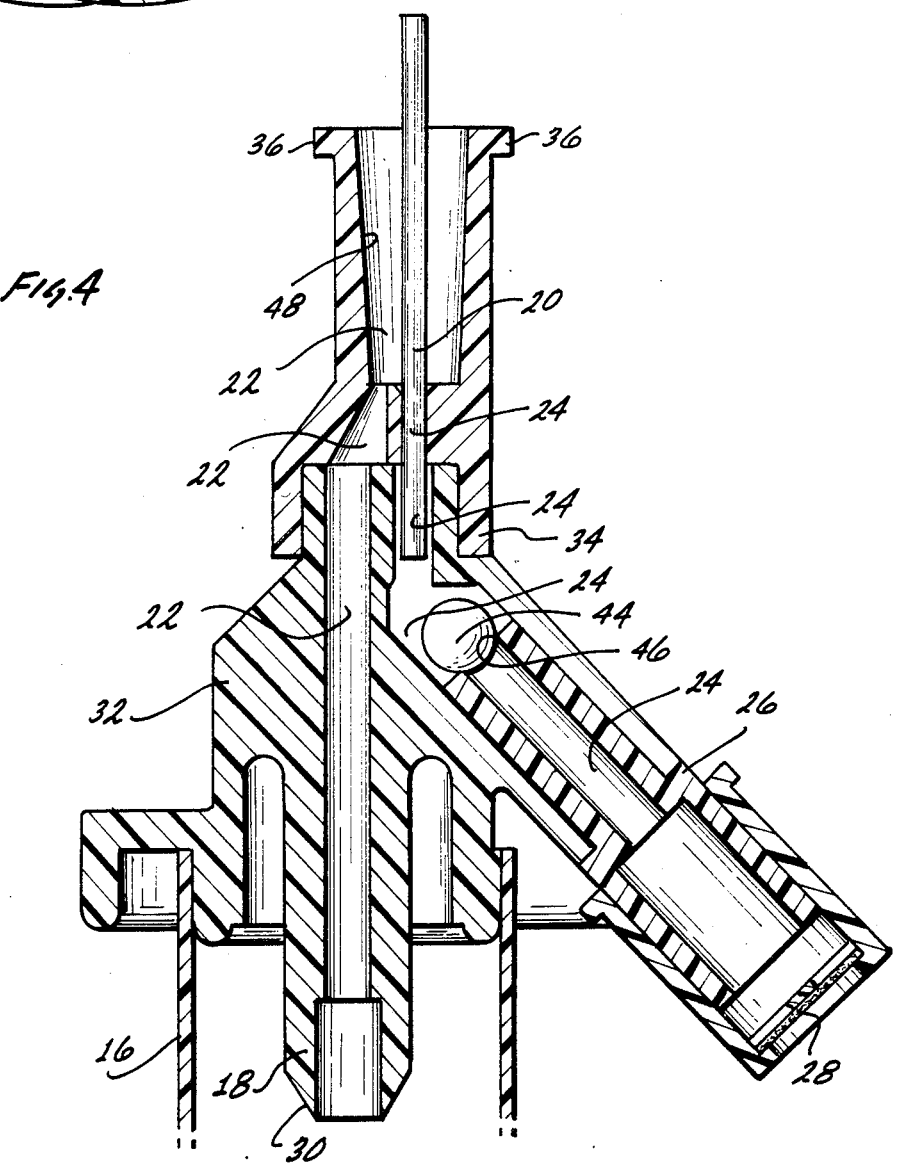
FIG. 4 is a cross-sectional view of the vented drip chamber as seen in FIG. 2 with the hypodermic syringe removed.

FIGS. 2 and 4 provide a detailed cross-sectional view of a portion of the drip chamber 10 of the particular structure for the drip chamber 10. Specifically, as seen in FIGS. 2 and 4, drip chamber 10 includes a transparent container 16 which is attached to a housing 32 by any means well known in the art. Formed onto housing 32 and extending into transparent container 16 of drip chamber 10 is a drop former 18. As will be appreciated by those skilled in the art, drop former 18 may be formed with a bevel 30 to assist in the formation of drops as fluid passes through drop former 18 and into transparent container 16. The sidewalls of container 16 are preferably made of a semi-rigid transparent material which will permit drip chamber 10 to be squeezed and thereby cause a partial filling of container 16 prior to operation of the administration set.

An adapter 34, shown in both FIG. 2 and FIG. 4, is formed with a fluid passageway 22. Adapter 34 is connected to housing 32 by any means well known in the art and is attached thereto in a manner to extend fluid passageway 22 through housing 32 to establish fluid communication between a fluid source such as the syringe 12 and drop former 18 in container 16.

Also formed into housing 32 and the adapter 34 is an air passageway 24. More specifically, as seen in FIG. 2 and FIG. 4, air passageway 24 is defined by a cannula 20 which is attached in fluid-tight relationship with the adapter 34 by any means well known in the art. With this attachment an air passageway 24 is defined from the hollow cannula 20 into the housing 32. Termination of the air passageway 24 is provided by an air filter 28 which can be of any type well known in the art and which is provided in the present invention to prevent contaminants from the atmosphere from entering into the fluid system. In the preferred embodiment, cannula 20 is made of a rigid material such as stainless steel.

As seen in FIGS. 2 and 4, ball valve 44 is disposed within the air passageway 24 of air filter housing 26. Ball valve 44 is positioned to provide an air seal at the point of contact between ball valve 44 and shoulder 46 in the air passageway 24 when fluid attempts to enter air passageway 24 from syringe 12. In this combination, ball valve 44 allows air or other gases to flow from outside drip chamber 10 through air passageway 24 and into syringe 12 to replace fluid which has been dispensed from syringe 12. As previously discussed, ball valve 44 also prevents fluid in syringe 12 from flowing through air passageway 24.

Figure 3:
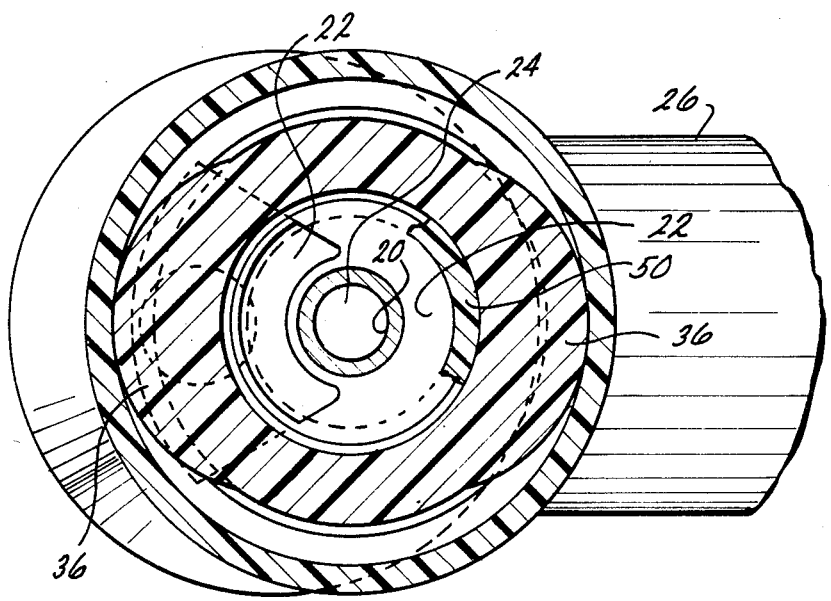
FIG. 3 is a cross-sectional view of the attachment between the vented drip chamber and the syringe as seen along the line 3—3 in FIG. 2.

Also seen in either FIG. 2 or FIG. 4 are ears 36 which are peripherally formed onto adapter 34 and which are suitable for engagement with a threaded luer adapter. As seen in FIGS. 2, 3 and 4, the ears 36 protrude peripherally and extend radially from adapter 34 and are engageable with threads 38 on connector extension 40 of syringe 12 for attachment of the syringe 12 with the adapter 34. Also, as best seen in FIG. 4, the adapter 34 is provided with a slight tapered region 48 which allows for an interference connection between the adapter 34 and the nozzle-shaped extension 50 of syringe 12 when adapter 34 is urged into extension 50.

OPERATION

In its operation, the drip chamber 10 is threadably engaged with the syringe 12 by rotating drip chamber 10 in a manner that permits nozzle-shaped extension 50 of syringe 12 to engage with adapter 34 as shown in FIG. 2. When rotated for this purpose, ears 36 on adapter 34 engage with threads 38 on connector extension 40 of syringe 12. Also, extension 50 urges into tapered region 48 of adapter 34 to provide for secure fluid tight engagement of adapter 34 with syringe 12. As best seen in FIG. 2, this engagement also causes the insertion of cannula 20 into the body of fluid contained in syringe 12. Further, engagement of the drip chamber 10 with syringe 12 in the manner above described establishes a fluid passageway 22 extending from the body of fluid contained in syringe 12 through the adapter 34 and on to the drop former 18 which is disposed in the transparent container 16 of drip chamber 10. A further appreciation of the geometry of fluid passageway 22 can be seen by reference to FIG. 3 which shows a portion of fluid passageway 22 in phantom.

FIG. 2 also shows that the connection of drip chamber 10 with the syringe 12 establishes an air passageway 24 from outside drip chamber 10 through air filter 28, air filter housing 26, adapter 34 and housing 32 to the body of fluid held in syringe 12. When drip chamber 10 is connected to syringe 12, the fluid contained in syringe 12 will attempt to enter cannula 20. However, as fluid attempts to enter cannula 20 from syringe 12, the increase in differential air pressure within air passageway 22 urges ball valve 44 against shoulder 46 in air passageway 24 to prevent the further flow of fluid from syringe 12 through air passageway 24. On the other hand, as fluid from syringe 12 drains through fluid passageway 22, ball valve 44 moves to permit air to enter through air filter 28 and into fluid passageway 22. The air entering through filter 28 continues through air passageway 24 and forms bubbles in the fluid contained in syringe 12. In the above described manner, the body of fluid contained within air-tight syringe 12 is vented to allow an uninterrupted, regular and predictable fluid flow through fluid passageway 22. It should also be noted that the above described operation permits the withdrawal of fluid from syringe 12 without a consequent moving of the plunger assembly 42 of syringe 12.

While the particular vented drip chamber for use with a syringe as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the apended claims.

I claim:

1. A vented drip chamber for engaging with a syringe comprising:

a container;

an adapter mounted on said container for engaging said drip chamber to said syringe, said adapter having a drop former disposed in said container and having a fluid passageway therethrough for fluid communication between said syringe and said drop former; and a cannula with a first end and a second end and having said first end attached to said adapter with said second end coaxially aligned within a portion of said fluid passageway and extending therefrom for insertion into said syringe for defining an air passageway to vent air from outside said drip chamber into said syringe.

2. A vented drip chamber as recited in claim 1 wherein said adapter is formed with means for threadably engaging said drip chamber with said syringe.

3. A vented drip chamber as recited in claim 2 further comprising:
   a ball valve disposed in said air passageway to allow air or other gases to flow into said syringe to replace the fluid which has been dispensed therefrom but does not allow fluid to flow out of said syringe via said air passageway.

4. A vented drip chamber as recited in claim 3 wherein said engaging means on said adapter comprises a plurality of protuberant ears peripherally oriented on said adapter and extending radially therefrom for threadable engagement with a syringe having compatible threading engagement means associated with its fluid exit port.

5. A vented drip chamber as recited in claim 4 wherein said container is made of a transparent semi-rigid plastic.

6. A vented drip chamber for observing the flow of a medical solution comprising:
   a container;
   an adapter attached to said container having a fluid passageway therethrough with a first end and an opposite end, said opposite end of said fluid passageway terminating in said container, and having an air passageway therethrough defined by a cannula having a first end and an opposite end, said first end of said cannula being coaxially aligned within said first end of said fluid passageway and said opposite end of said cannula in air communication to the outside of said container;
   a fluid source for holding the medical solution; and
   means formed on said adapter for threadably engaging said drip chamber with said fluid source to position said first end of said fluid passageway and said first end of said cannula in the fluid source to establish fluid communication between said fluid source and said container via said fluid passageway and to vent air into said fluid source from outside said container via said air passageway.

7. A vented drip chamber as recited in claim 6 wherein said fluid source is a syringe for collecting a precisely measured quantity of medical solution.

8. A vented drip chamber as recited in claim 7 further comprising:
   a cannula mounted on said adapter for extending said air passageway into said syringe.

9. A vented drip chamber as recited in claim 8 wherein said syringe is formed with a nozzle-shaped extension for dispensing fluids and said cannula is of sufficient length to extend through said nozzle-shaped extension to terminate within said syringe when said drip chamber is threadably engaged with said syringe having compatible threading engagement means associated with its fluid exit port.

10. A vented drip chamber as recited in claim 9 wherein said cannula is metal.

11. A vented drip chamber as recited in claim 10 wherein said engaging means on said adapter comprises a plurality of protuberant ears peripherally oriented on said adapter and extending radially therefrom for threadable engagement with a syringe.

12. A vented drip chamber as recited in claim 11 further comprising:
   a ball valve disposed in said air passageway to allow air or other gases to flow into said syringe to replace the fluid which has been dispensed therefrom but does not allow fluid to flow out of said syringe via said air passageway.

13. A vented drip chamber as recited in claim 12 further comprising:
   a drop former extending from said adapter for terminating said fluid passageway within said container.

14. A vented drip chamber as recited in claim 13 wherein said cannula is spaced from at least a portion of the inside surface of said nozzle-shaped extension to permit fluid flow therebetween.

15. A vented drip chamber adapted for engagement with a syringe wherein said syringe has a threaded engagement means and an associated nozzle-shaped extension for dispensing fluids comprising:
   a container;
   an adapter mounted on said container having a drop former disposed in said container and having first and second passageways formed therethrough, said first passageway defining a fluid path between said syringe and said drop former and said second passageway defining an air path to vent air from outside said drip chamber into said syringe;
   an engaging means formed on said adapter comprising a plurality of protuberant ears peripherally oriented on said adapter and extending radially therefrom for threadable engagement with said syringe;
   a ball valve disposed in said second passageway to allow air or other gases to flow into said syringe to replace the fluid which has been dispensed therefrom, but does not allow fluid to flow out of said syringe via said second passageway; and
   a rigid cannula having a first end and a second end and having said second end attached to said adapter with said first end coaxially aligned within a portion of said first passageway for extending said second passageway into said syringe through said nozzle-shaped extension of said syringe and spaced from at least a portion of the inside of said nozzle-shaped extension to permit fluid flow therebetween.

* * * * *